US008790279B2

(12) United States Patent
Brunner

(10) Patent No.: US 8,790,279 B2
(45) Date of Patent: Jul. 29, 2014

(54) GAIT ANALYSIS SYSTEM

(75) Inventor: Wolfgang Brunner, Maierhoefen (DE)

(73) Assignee: Zebris Medical GmbH (DE)

( * ) Notice: Subject to any disclaimer, the term of this patent is extended or adjusted under 35 U.S.C. 154(b) by 712 days.

(21) Appl. No.: 12/270,074

(22) Filed: Nov. 13, 2008

(65) Prior Publication Data

US 2009/0124938 A1  May 14, 2009

(30) Foreign Application Priority Data

Nov. 14, 2007 (DE) .................. 10 2007 054 365

(51) Int. Cl.
| | |
|---|---|
| A61B 5/103 | (2006.01) |
| A61B 5/117 | (2006.01) |
| A63B 71/00 | (2006.01) |
| A63B 22/02 | (2006.01) |
| A63F 9/24 | (2006.01) |
| A63F 13/00 | (2014.01) |
| G06F 17/00 | (2006.01) |
| G06F 19/00 | (2011.01) |

(52) U.S. Cl.
USPC ............ 600/595; 600/587; 600/592; 482/8; 482/9; 482/54; 463/6; 463/7

(58) Field of Classification Search
USPC ......... 600/587, 592, 595; 482/2–6, 8, 9, 54, 482/66, 74; 702/150–154; 463/6, 7, 23; 472/48; 73/670
See application file for complete search history.

(56) References Cited

U.S. PATENT DOCUMENTS

| | | | | |
|---|---|---|---|---|
| 4,278,095 | A * | 7/1981 | Lapeyre | 600/502 |
| 5,205,800 | A * | 4/1993 | Grant | 482/54 |
| 5,299,454 | A | 4/1994 | Fuglewicz et al. | |
| 5,474,087 | A * | 12/1995 | Nashner | 600/595 |
| 5,667,459 | A * | 9/1997 | Su | 482/4 |
| 6,033,344 | A | 3/2000 | Trulaske et al. | |
| 6,645,126 | B1 * | 11/2003 | Martin et al. | 482/54 |
| 6,796,927 | B2 * | 9/2004 | Toyama | 482/8 |
| 6,878,100 | B2 * | 4/2005 | Frykman et al. | 482/54 |
| 6,916,273 | B2 * | 7/2005 | Couvillion et al. | 482/8 |
| 7,387,592 | B2 * | 6/2008 | Couvillion et al. | 482/8 |
| 2003/0211896 | A1 | 11/2003 | Wang et al. | |
| 2004/0147369 | A1 * | 7/2004 | Jimenez Laso | 482/8 |
| 2004/0192511 | A1 * | 9/2004 | Ein-Gal | 482/54 |
| 2006/0247096 | A1 * | 11/2006 | Raniere | 482/1 |
| 2006/0247104 | A1 | 11/2006 | Grabiner et al. | |
| 2007/0060451 | A1 * | 3/2007 | Lucas | 482/54 |
| 2007/0298937 | A1 * | 12/2007 | Shah et al. | 482/54 |
| 2008/0221487 | A1 * | 9/2008 | Zohar et al. | 600/595 |

* cited by examiner

Primary Examiner — Devin Henson
(74) Attorney, Agent, or Firm — Donald R. Boys; Central Coast Patent Agency, Inc.

(57) ABSTRACT

A gait analysis system for training or rehabilitation has an endless belt with pressure sensors underneath the belt to sense a person walking on the belt and an analyzing unit for analyzing the gait of the person. The system further includes an image display system with stored data for displaying images to a person using the apparatus training and/or therapy purposes.

15 Claims, 3 Drawing Sheets

GAIT ANALYSIS SYSTEM

CROSS-REFERENCE TO RELATED DOCUMENTS

Figure 1:
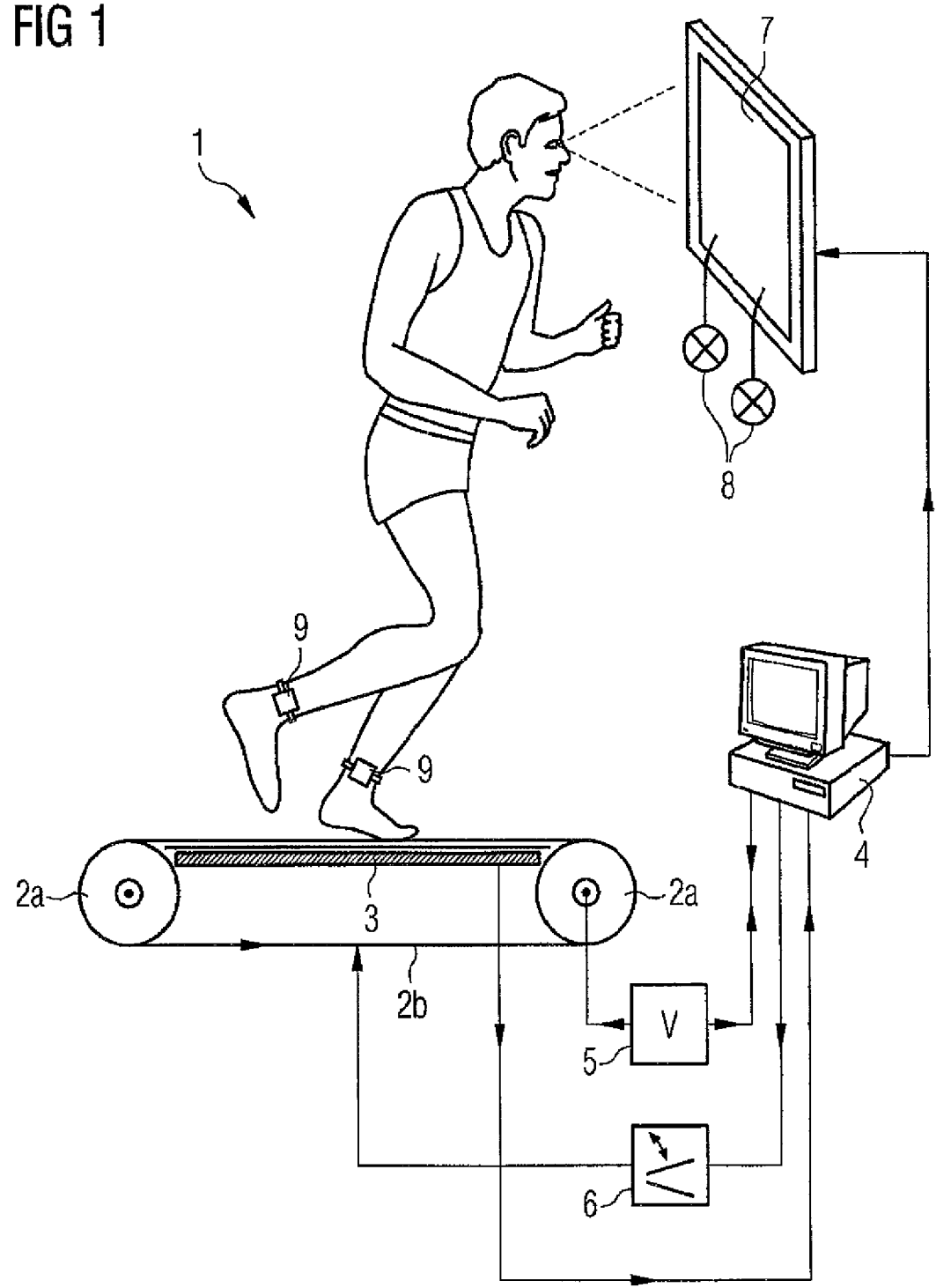

The present application claims priority to a German patent application serial number DE 10 2007 054 365.6, filed on Nov. 14, 2007, which is incorporated herein in its entirety, at least by reference.

The present invention relates to a gait analysis system for training or rehabilitation purposes.

Apparatus for the detection of pressure and force distributions are known per se, for example, from DE 36 42 088 C2 and DE 25 29 475 C3.

Many of the prior apparatus can be employed as platforms for the biomechanical gait analysis, which examine and analyze the gait of a vertebrate, especially of a human being, but also of a horse or dog etc., if necessary. There is the drawback, however, that only one single step and one single flexing action of the foot can be recorded. To obtain a natural gait behavior it is necessary, however, to record the gait over a longer time period.

Therefore, apparatus and methods for the gait analysis using a treadmill have already been proposed. Reference is here made, for example, to DE 40 27 317 C1 or U.S. Pat. No. 6,010,465 A.

Moreover, a measuring device is described as being known in R. Kram and A. J. Powell: "A treadmill-mounted force platform" Appl. Physiol. 67 (4): 1692-1698 (1989), wherein a treadmill belt is drawn over a measuring platform or measuring surface, respectively, thereby permitting a continuous detection of forces.

The first one of these publications describes a treadmill formed of a plurality of members, each of which comprises pressure or force sensors, respectively, which are arranged in a matrix, while the second publication describes a treadmill comprising a measuring plate disposed underneath the belt surface with pressure or force sensors, respectively, arranged in a matrix. Both publications teach that an analyzing unit is connected to the respective sensor system, and U.S. Pat. No. 6,010,465 describes relatively detailed the construction and the operating mode of the analyzing unit, for example, for analyzing the position and an associated force quantity when stepping onto the treadmill belt, e.g. for determining torsional moments and loads exerted on the ankle joints, as well as specific gait parameters.

The international patent application PCT/EP2006/01 04 71 of the Applicant deals with improvements of said prior solutions in view of the derivation of differentiated medical and sports-physiological statements. This patent application particularly discloses means and methods for the precise and differentiated detection of the actual speed of the treadmill based on the time- and position-dependency of pressure distribution images recorded on it as a subject is walking or running.

Further known is the use of display devices, such as display screens, in treadmill systems.

Known from EP 1 145 682 A2 are a rehabilitation apparatus and method based on the treadmill technology, wherein an adaptation of the function of the treadmill to the current status of a patient's walking or running ability to be restored is provided. Specifically, the speed of the treadmill belt is adapted to a personal step cycle of the user, and the apparatus is to give the user a feedback at the same time. In a specific embodiment, also the detection of pressure forces exerted during a step as well as the analysis thereof are provided as part of an overall program. The publication also describes the use of a display screen in connection with a keyboard, to display the footprints generated on the treadmill belt and to adjust treadmill belt parameters on the basis of this display.

U.S. Pat. No. 6,231,527 B1 likewise discloses the use of a display screen in a treadmill apparatus for use in sports medicine and rehabilitation, wherein the images of different cameras can be displayed, which record the movements of the sportsman/patient on the treadmill.

The invention is based on the object to provide a further improved apparatus of the above-defined type, which is particularly suited for sports-medical and rehabilitation purposes. It is an object to apply the treadmill with an integrated pressure distribution sensor system not only as a pure analyzing apparatus for analyzing the standing at rest, the walking and running, but to further develop the system to achieve a training/therapy apparatus.

This object is achieved with a gait analysis system comprising the features of claim 1 and, according to a relatively independent development of the inventive concept, with a system according to claim 4. Useful embodiments of the inventive concept are defined in the dependent claims.

The system according to the invention permits the recording of the gait over a longer period of time because a treadmill system is used. This treadmill system comprises an endless belt drawn over a sensor platform, which is provided with a plurality of pressure and force sensors arranged in a matrix.

Essential aspects and embodiments of the invention are:

First, the known treadmill comprising a pressure distribution sensor system is additionally provided with a computer unit and display/indication means, such as a display screen and/or an acoustic feedback device. In one embodiment, a load analysis is performed, whereby the subject/examiner is warned by a feedback signal when the weight load exceeds a certain extent. To this end, the patient is hung up, for example, by a weight relief and belt system.

In a simplification of the known pressure distribution matrix it may be sufficient that the same only consists of a matrix of On/Off switches, which do not detect analog pressure/force values, but only two switching states. A possibly variable switching resistor could hereby be used to perform the initially described load feedback.

In another embodiment the system can make a difference between the load exerted on the left and right leg. In a simple embodiment this may be accomplished by locally dividing the treadmill belt or the pressure distribution sensor system, respectively, into a left and right area If the load exerted on one leg is exceeded, this is indicated, for example, by an audio signal. Thus, it can be trained to load one leg with only a certain percentage of the body weight, for example, after a hip joint operation. To this end, it is sensible that the patient can reduce the weight by means of a handrail or an armrest. To determine the allowable share of the load, either the body weight can be inputted prior to the measurement, or the total body weight is initially measured by the sensor system provided in the treadmill.

In another embodiment the subject is assigned tasks relating to and influencing his walking/running. For example, the subject runs on a simulated forest track and has to avoid water puddles depicted on the floor. If he steps into the "water", this is detected and displayed. A corresponding analysis shows the success rate.

In addition to the playful effect and the effect that the coordination is improved, this kind of feedback also has the advantage that different variations of footsteps are provoked, which will lead to a better diagnosis and to better possibilities for the production of orthopedic insoles. The reason is that normal walking on the treadmill belt results in an ingrained, stereotypic walk, which might not reveal a walking disorder. In a preferred embodiment the speed of the treadmill belt as well as the angle of inclination of the belt are controlled by a computer unit. This provides for additional provocation possibilities and permits, again, a direct analysis of the changed behavior of walking and flexing one's foot.

In another embodiment it is provided to integrate either stationary elevations and recesses, respectively, or actuators into or underneath the walking surface, by means of which raised areas can be realized on the walking surface. This could be realized, for example, with a matrix of air- or fluid-filled chambers, which are likewise controlled by the computer unit and which may be used for provocation tests.

In the first modification it is particularly expedient if the endless belt having a gait-effectively structured surface is provided with a position coding to assign the position of surface elements, if the processing unit comprises profile storage means for storing the profile of the gait-effectively structured surface and is assigned a position signal receiver for addressing the profile storage means, and if a processing algorithm is implemented in the processing unit, by means of which the pressure distribution images are assigned to the surface elements of the walking surface.

An advantageous embodiment of the second modification is characterized in that the assembly of actuators is assigned a profile control unit, which outputs control signals for actuating the actuators to form a predetermined dynamic profile of the walking surface, that the processing unit comprises a control signal receiver for receiving the control signals outputted by the profile control unit as position assignment signals and that a processing algorithm is implemented in the processing unit, by means of which the pressure distribution images are assigned to the dynamic profile of the walking surface.

Specific constructive means used to deform the belt surface may be mechanical, electromechanical, hydraulic or pneumatic constructions known per se, which can particularly be controlled by electric control signals with a sufficient response characteristic. Examples are that the assembly of actuators comprises a plurality of individually driven lifters to produce elevations on the walking surface, or that in the endless belt or underneath the walking surface an assembly of chambers is provided to form elevations on the walking surface, said chambers having a controllable fluid connection and being elastically expandable by the fluid pressure.

A relatively independent basic idea of the invention resides in providing a treadmill system known per se with the following additional components: an image display surface assigned to the treadmill and arranged in the field of view of the subject, a film or video reproducer with visual material stored in a visual material storage means or a connection to connect a visual material database for receiving visual material to simulate a walking environment and/or to illustrate demands on, questions or the like to the subject, and a synchronization stage for synchronizing the processing of the pressure distribution images with the illustrations on the image display surface.

The realization of the image display surface, in connection with the film or video reproducer, can be accomplished with a plurality of commercially available components known per se, whereby the purpose and the equipment level of the system as proposed play a significant role. In a simple embodiment the film or video reproducer is represented by a PC or a television receiver, the screen of which serves as image display surface. A more complex embodiment permitting a more realistic simulation of natural walking environments is characterized in that the film or video reproducer comprises a laser beamer and the image display surface is embodied by a projection surface.

The two basic realizations of the inventive concept can expediently be extended by also simulating ascending and descending walking routes. To this end, inclination adjustment means are provided to adjust the inclination of the treadmill, and in the realization including a visual simulation of a natural walking environment corresponding visual material is generated and played in coordination with the adjusted inclination of the treadmill.

Basically in analogy with this, speed adjusting means to adjust the speed of the treadmill belt are provided in another embodiment, and, in this case, too, the simulation offered to the subject can be coordinated with the current speed of the treadmill belt. Also, both adjustment possibilities may sensibly be combined, and particularly it is provided that the synchronization stage can be programmed with data, which are based on the visual material or the demands on, questions or the like to the subject, in such a way that the processing of the pressure distribution images can be accomplished on the basis of corresponding defaults. For example, the subject may be instructed in the illustration not to step on certain areas of the walking route (i.e. of the treadmill belt), and it will be checked in an analysis of the pressure distribution images coordinated therewith whether he has succeeded in doing so, as requested.

In another embodiment of the invention the system is provided with additional measuring means for detecting at least a second biometrical or medical measured quantity, wherein the processing unit is designed to perform the combined processing of the pressure distribution images and of measured values of the additional biometrical measured quantity. Expediently, a synchronization unit for synchronizing the pressure/force distribution measurement with the detection of the or another biometrical or medical measured quantity carried out by the additional measuring means is then additionally provided. In one modification of this embodiment, moreover, the synchronization unit is connected, on the input side, to the analyzing or processing unit in such a way that synchronization signals are outputted in response to features of the pressure distributions or the values or signals derived therefrom, respectively.

Another sensible embodiment of the invention provides that the visual material for the simulation of a walking environment and/or for the illustration of demands, questions or the like is coordinated with the gait-effectively structured surface of the endless belt, and that the film or video reproducer and the treadmill belt are synchronized by a surface/image synchronization stage so as to ensure a coordination in terms of time. More specifically it can be provided that the surface/image synchronization stage and the synchronization stage for synchronizing the processing of the pressure distribution images are programmable in such a coordinated manner that the processing of the pressure distribution images includes both the current gait-effective surface elements of the walking surface and image contents coordinated therewith, which are shown to the subject as he is walking or running.

To obtain a convincing simulation of natural walking environments and utilizable results, it is important that the illustrated simulation (screen projection) is coordinated with the current speed of the treadmill belt sufficiently precisely, and especially that an increasing time shift is avoided as the duration of the exercise increases. On the one hand, this can be achieved by a manual input of a preselected treadmill belt speed and by keeping constant both the speed of the treadmill belt and the readout rate. However, more flexible is a solution according to which the current treadmill belt speed is continuously detected and the readout rate is controlled in response thereto.

The belt speed can be detected by a measurement of the rotational speed of the roller driving the belt or by the detection of the propagation speed of certain, specifically provided patterns (codings) on the lower side or the upper side of the belt, or also by means of a pattern recognition of the pressure distribution images generated by the user on the pressure sensor matrix, which is described in more detail in the earlier patent application PCT/EP2006/010471.

Figure 2:
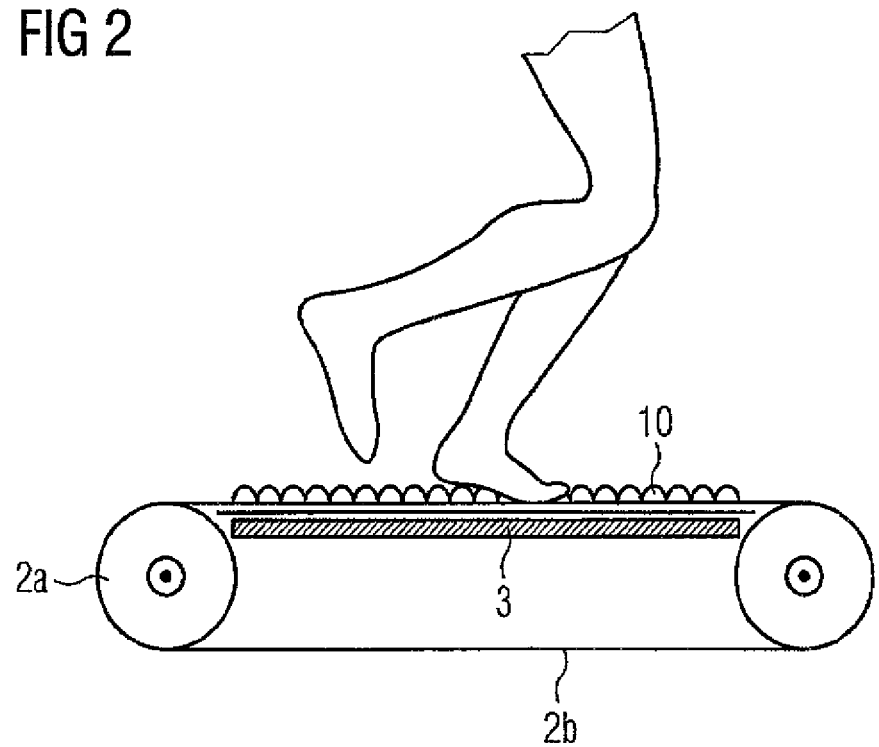
Figure 3:
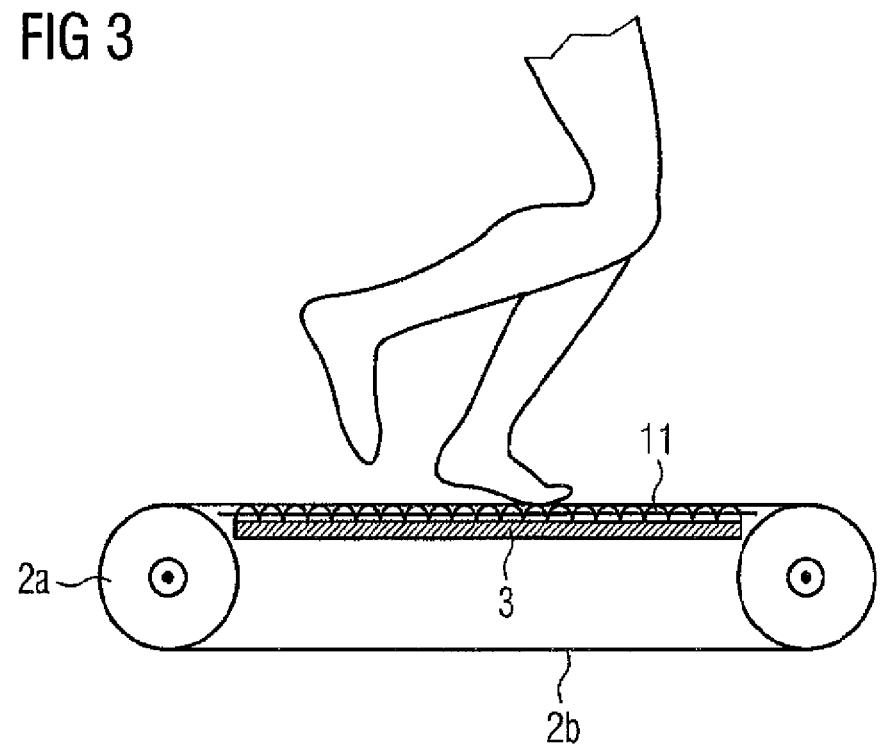
Figure 4:
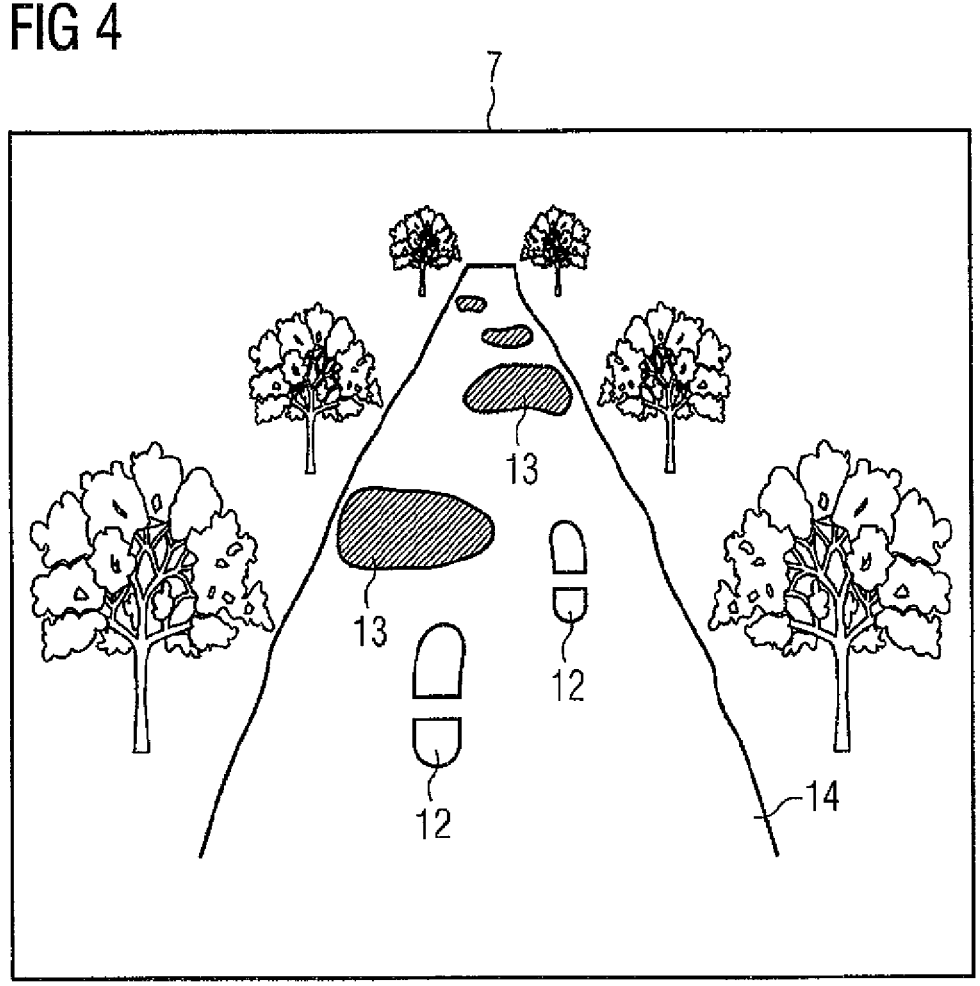

The person skilled in the art will appreciate that the above-outlined device aspects of the invention correspond, at the same time, to the method aspects, so that a separate listing can be omitted. In other respects, too, the implementation of the invention is not limited to the above-defined specific aspects and embodiments, but is also feasible in a plurality of modifications lying within the scope of the knowledge of the person skilled in the art. Advantages and expediencies of the invention are defined in the following description of some embodiments by means of the figures. In the figures:

FIG. 1 shows a sketch-like representation of an exemplary total system of the type according to the invention, FIGS. 2 and 3 show sketch-like representations of embodiments of the treadmill belt for the realization of an effectively structured surface, and FIG. 4 shows a sketch-like representation of a screen image projected for a user of the system.

FIG. 1 shows a treadmill training system 1, comprising a treadmill belt 2b running over two rollers 2a, under the upper surface of which, which is used by the user, a pressure detection plate 3 with a high spatial resolution and having a plurality of (not individually designated) pressure sensors is provided, which pressure sensors are arranged in a matrix-type manner and detect pressure detection images generated by the user as he steps on the treadmill belt. One of the two rollers 2a is driven and pulls the belt 2b at a predetermined speed, which is adjusted by a processing and control unit 4 of the system and by a speed controller 5. According to another significant operating parameter of the system it is possible to adjust (this is merely symbolically illustrated in the figure) by means of a suited inclination actuator 6, which can likewise receive interference signals from the processing and control unit 4, an inclination of the treadmill belt according to need.

In the embodiment illustrated in FIG. 1, which is strongly simplified, signals characterizing the adjusted speed value of the treadmill belt are reported back from the speed controller 5 to the processing and control unit 4, where they serve the synchronization of an illustration on a display screen 7, which is placed in the visual field of the user and shows the user a simulation of a natural walking route. The illustration is controlled by the speed signals in such a way that—especially in connection with another specific embodiment described below—the user is presented an altogether harmonious simulation of a walking environment, preferably coupled with the simulation of obstacles to be overcome or avoided. Diverging from the representation in the figure, also the actual speed of the treadmill belt can be detected by an appropriate (non-illustrated) sensor system and the measured value be supplied to the processing and control unit 4 for the same purpose.

In a specific embodiment of the speed adjustment it may be considered that a human being does not maintain a completely constant instantaneous speed, even if he walks uniformly. With regard to this, the system as illustrated can slightly vary the speed of the belt, optionally even at each step, in response to the flexing pattern of the feet, which is detected by the pressure detection plate 3. Thus, during the flexing phases of the left and right foot, the belt speed can be slightly reduced or increased, respectively. These slight variations of the belt speed provide the user with feedbacks, encouraging him to walk on the treadmill belt more naturally.

Optionally, the pressure sensors of the pressure detection plate may have an analog or—in a simplified and more inexpensive embodiment—a digital operating characteristic (off/on characteristic). Both types have their justifications for specific applications, and the system designer will choose one of the options in accordance with the primary use requirements.

Instead of the screen 7 schematically represented in FIG. 1, also an assembly of several screens, which partially surround the user, or a video projection device (laser beamer etc.) may be provided. As is shown in the figure, the display surface serving the simulation may be supplemented with information and warning indicators 8, respectively, which request the user to perform or cease certain activities. Such indicators can request him, for example, to deliberately step onto a defined surface of the treadmill belt or enter into a highlighted surface area in the simulation of the walking environment, or to avoid the same. In connection with this, such indicators can then directly provide the user with feedbacks about the success of his efforts. These indicators can partially also realize audible indications and can be combined with them.

For performing training tasks on the treadmill system it may be of interest to detect the lifting height of the feet from the belt, for example, if the subject is to climb over a virtual obstacle. In another embodiment the subject therefore has at least one sensor 9 attached to one foot, the signals of which can be detected by means of a (non-illustrated) position detection sensing system, which is known per se, so as to draw conclusions on the position or the height of the feet, respectively. Preferably, the sensors are operated time-synchronized with the sensors of the pressure distribution matrix. If appropriate, a precise time synchronization can be generated by means of an infrared or radio signal, or by a detection of the moment when the feet contact the belt.

The sensors 9 may be designed as acceleration sensors or multi-axis acceleration sensors and, if appropriate, are wirelessly connected to the analyzing computer 4. The position of the feet can be calculated from the acceleration signals, especially if the time and position dependency of the pressure distribution pattern can be additionally included in the calculation. In extended systems, inertial sensor systems may be employed, in which gyroscopes or sensors to detect the earth magnetic field are used additionally. Of course, such sensors can also be attached to other body sections, so that the movement of the complete lower extremities or of the whole body can be measured and represented. However, the sensors 9 may also be operated in accordance with other measuring principles, e.g. on the basis of active or passive light markers recorded by stationary cameras, magnetic field sensors or sensors emitting or receiving ultrasonic waves to or from stationary receivers and determining the position of the feet from the propagation time of the sound.

FIG. 2 shows an embodiment in which a structured surface is achieved with actuators 10. The actuators 10 are located in the treadmill belt 2b and are moved over the rollers of the treadmill system 2. They are preferably activated when they appear on the upper walking surface. In the embodiment, fluid- or air-filled chambers are illustrated. These can be formed as complete rows or as individual matrix-type arranged chambers.

In FIG. 3 the actuators 11 are disposed underneath the treadmill belt 2b. The belt glides over the actuators 11. As is shown in FIG. 2 and 3, the forces are transmitted via the actuators to the pressure distribution sensor matrix 3. If the actuators shown in FIGS. 2 and 3 are integrated in the treadmill training system of FIG. 1, it is possible to simulate largely natural walking conditions. It is possible to illustrate different ground conditions in the virtual walking environment on the display unit. For example, a stone can be virtually illustrated on the walking route. The subject sees the stone on the display unit together with his footprints, can avoid the same or feels the stone via the actuators when he steps on it. In the field of rehabilitation this system according to the invention permits the patient to get used to walking in a natural environment and to train the walking in a natural environment, respectively, without the risk of falling over.

FIG. 4 shows an embodiment of a virtual walking environment, as can be displayed on the display unit 7. On a virtual walking route 14 the prints 12 of the pressure distribution measuring sensors 3 are visible. These preferably move synchronously with the actual footprints of the subject on the belt. In a preferred embodiment, the walking route 14 moves at a speed synchronized with the speed of the belt.

The footprints 13 may be illustrated as contours, as artificial sole prints, as actual pressure distribution images both two- and three-dimensionally. If appropriate, also three-dimensional models in the form of feet or shoes or any other shape may be displayed. It is likewise possible to control with the feet on the belt virtual objects on wheels, e.g. a bicycle or a car, or an object on skids. In the illustration of FIG. 4, the walking route 14 includes virtual areas 13 which must not be stepped on. These may be illustrated, for example, as water puddles. It is also possible to show (simulate) other surfaces or physical objects, such as pits, rocks, obstacles and the like.

In another embodiment the areas 13 are to be stepped on, while the surrounding areas of the walking route 14 are not stepped on. The areas 13 can either appear according to the random principle and in different shapes, or in like shapes and/or at regular intervals. If appropriate, it may also be requested to modify the press-on pressure of the feet on the belt, or the belt speed may be varied if, for example, the press-on pressure is higher or lower. In the same way it is possible to control the simulation of the walking environment if the pressure distribution on the belt deviates from a normal flexing action of the feet.

To check the success of the tasks assigned, the system according to the invention reports back a feedback signal. In the embodiment of FIG. 4 this may be accomplished by a different color or a motion of the water surface if the virtual puddle is stepped into. If appropriate, points may be credited to or deducted from a point account to control the success. To receive a success feedback if the assigned task was accomplished, moreover, the most various possibilities of visual or audible feedback may be applied.

In a preferred embodiment in the field of rehabilitation, the patient having gait disorders is given virtual areas on which he has to place his feet step by step. The treadmill training system checks the actually made steps and can provide information by audible or visual feedback, or possibly even by a voice output, whether the steps were properly made or what can be made better.

Preferably, the measured pressure distribution values of the steps of each flexing action made on the treadmill belt are stored temporarily in the analyzing computer 4. Thus, the pressure distribution images can be analyzed already during or after a measurement and may be used for diagnostic purposes or for producing orthopedic insoles.

In these or similar applications it is particularly advantageous that the assigned tasks provide for a greater variability of the pressure distribution images, as compared to a result obtained with an "ingrained" gait on the treadmill belt. A particular application relates to preventing elderly people from falling over. It is well known that the risk of elderly people falling over while walking increases if they have to cope with two tasks at the same time. In order to test this risk of falling over, yet an additional task is surprisingly introduced for the subject on the walking route, which has to be coped with. For example, virtual objects or dangers may show up. Then, modifications in the gait security can be derived from the analysis of the dynamic pressure distribution images.

The invention claimed is:

1. A gait analysis system for training and rehabilitation purposes, comprising:
    an endless belt guided over at least two rollers and serving as a treadmill belt, wherein the upper surface serves as a walking surface;
    a sensor system for determining a pressure/force distribution on a force measurement plate located underneath the walking surface, the force measurement plate having a plurality of pressure/force sensors facing the endless belt;
    an analyzing unit connected, on an input side to the pressure/force sensors, the analyzing unit detecting pressure distributions generated on the walking surface by a user's feet contacting the endless belt, while the endless belt is in motion, by a subject walking or running on the endless belt;
    a processing unit connected to the analyzing unit, the processing unit generating actual pressure distribution images of each footprint of the user's feet while contacting the endless belt;
    an image display screen arranged in a field of view of the subject;
    a film or video reproducer with visual material stored in a visual material storage repository or a connection to connect a visual material database for receiving and displaying the visual material on the display screen as a moving virtual route, and a synchronization stage for synchronizing the actual pressure distribution images with the moving virtual route displayed on the display screen;
    wherein, as the user walks or runs on the endless belt, the moving virtual route is displayed to the user synchronized with the footprints of the user.

2. The system according to claim 1, wherein the film or video reproducer is represented by a PC or a television receiver having a screen serving as the image display screen.

3. The system according to claim 1, wherein the film or video reproducer comprises a laser beamer and the image display surface is embodied by a projection surface.

4. A gait analysis system for training or rehabilitation purposes, comprising:
    an endless belt guided over at least two rollers and serving as a treadmill belt, the endless belt comprising one or both of a pattern of deformities in the belt itself, or an assembly of actuators underneath the belt, the actuators managed to provide deformities in a walking surface of the belt;
    a sensor system for determining a pressure/force distribution on a force measurement plate located underneath the walking surface, the force measurement plate having a plurality of pressure/force sensors facing the endless belt, an analyzing unit connected to the pressure/force sensors, the analyzing unit detecting pressure distributions generated on the walking surface by a user's feet contacting the endless belt, a processing unit connected to the analyzing unit, the processing unit generating actual pressure distribution images of each footprint of the user's feet while contacting the endless belt;

a display screen arranged in a field of view of the subject;

a film or video reproducer with visual material stored in a visual material storage repository or a connection to connect a visual material database for receiving and displaying the visual material on the display screen as a moving virtual route, the visual material including images of the pattern of deformities in the endless belt; and a synchronization stage for synchronizing the actual pressure distribution images synchronized with the moving virtual route displayed on the display screen;

wherein, as the user walks or runs on the endless belt, the moving virtual route is displayed to the user synchronized with the actual pressure distribution images of the user and synchronized with the pattern of deformities in the endless belt.

5. The system according to claim 4, wherein the endless belt is provided with a position coding to assign position of deformities, the processing unit comprises a profile storage repository for storing a profile of the pattern of deformities and is assigned a position signal receiver for addressing the profile storage repository, and a processing algorithm is implemented in the processing unit, whereby the actual pressure distribution images are assigned to surface elements of the walking surface.

6. The system according to claim 4, wherein the assembly of actuators is assigned a profile control unit outputting control signals for actuating the assembly of actuators to form a predetermined dynamic profile of the walking surface;

the processing unit comprises a control signal receiver for receiving the control signals outputted by the profile control unit as position assignment signals; and a processing algorithm is executed in the processing unit, whereby the actual pressure distribution images are assigned to the predetermined dynamic profile of the walking surface.

7. The system according to claim 4, wherein the assembly of actuators comprises a plurality of individually driven lifters to produce elevations on the walking surface.

8. The system according to claim 4, wherein in the endless belt an assembly of chambers is provided to form elevations on the walking surface, said assembly of chambers having a controllable fluid connection and being elastically expandable by fluid pressure.

9. The system according to claim 4, comprising an inclination adjustment mechanism to adjust inclination of the treadmill endless belt, and/or~speed adjust mechanism to adjust running speed of the treadmill endless belt.

10. The system according to claim 9, wherein the inclination adjustment means and/or the speed adjustment means are synchronized with a film or video reproducer in such a way that the inclination and adjustment mechanism and speed adjustment mechanism, respectively, perform in coordination with visual material illustrated to the subject and/or demands on or questions to the subject.

11. The system according to claim 10, wherein synchronization can be programmed with data based on visual material illustrated to the subject and/or demands on or questions to the subject, in such a way that processing of the actual pressure distribution images can be accomplished on a basis of corresponding defaults.

12. The system according to claim 10, wherein visual material for the simulation of a walking environment and/or for the illustration of demands and questions is coordinated with the pattern of deformities in the endless belt, and the film or video reproducer and the treadmill endless belt are synchronized by a surface/image synchronization stage so as to ensure a coordination.

13. The system of claim 4, comprising an additional measuring mechanism for detecting at least a second biometrical or medical measured quantity, wherein the processing unit is designed to perform the combined processing of the actual pressure distribution images and of measured values of the second biometrical or medical measured quantity.

14. The system according to claim 13, wherein a synchronization unit is provided for synchronizing the pressure/force distribution measurement with the detection of the second biometrical or medical measured quantity carried out by the additional measuring mechanism.

15. The system according to claim 14, wherein the synchronization unit is connected to the analyzing or processing unit such that synchronization signals are outputted in response to features of the pressure distributions or the values or signals derived therefrom, respectively.

* * * * *